(12) United States Patent
Edelmann et al.

(10) Patent No.: US 8,467,069 B2
(45) Date of Patent: Jun. 18, 2013

(54) METHOD AND DEVICE FOR INSPECTING THE QUALITY OF A FORMED THERMOPLASTIC FIBER-REINFORCED PLASTIC COMPONENT

(75) Inventors: Klaus Edelmann, Bremen (DE); Tanja Frese, Horstedt (DE); Carsten Brandt, Bremen (DE); Jens Kethler, Weyhe (DE); Christoph Von Kopylow, Wilstedt (DE)

(73) Assignee: Airbus Operations GmbH (DE)

( * ) Notice: Subject to any disclaimer, the term of this patent is extended or adjusted under 35 U.S.C. 154(b) by 0 days.

(21) Appl. No.: 13/403,386

(22) Filed: Feb. 23, 2012

(65) Prior Publication Data

US 2012/0170051 A1 Jul. 5, 2012

Related U.S. Application Data

(63) Continuation of application No. PCT/EP2010/005156, filed on Aug. 23, 2010.

(60) Provisional application No. 61/237,384, filed on Aug. 27, 2009.

(30) Foreign Application Priority Data

Aug. 27, 2009 (DE) .......... 10 2009 038 746

(51) Int. Cl.
*G01B 11/30* (2006.01)
(52) U.S. Cl.
USPC ......... 356/600; 356/607; 356/239.7; 356/608

(58) Field of Classification Search
USPC .......... 356/239.7, 600, 607–608, 227.25
See application file for complete search history.

(56) References Cited

U.S. PATENT DOCUMENTS

| 4,792,232 | A | 12/1988 | Jobe et al. |
| 6,657,429 | B1 * | 12/2003 | Goldfine et al. ............. 324/232 |
| 7,307,714 | B2 * | 12/2007 | Cyr et al. ................... 356/239.8 |
| 7,570,794 | B2 | 8/2009 | Swanger et al. |
| 2007/0035733 | A1 | 2/2007 | Reich et al. |
| 2007/0107520 | A1 | 5/2007 | Vaccaro et al. |
| 2008/0192987 | A1 | 8/2008 | Helgason et al. |

FOREIGN PATENT DOCUMENTS

| DE | 4106334 C1 | 7/1992 |
| DE | 10258336 B3 | 4/2004 |
| DE | 102006040365 A1 | 5/2007 |
| WO | 02061368 A2 | 8/2002 |

* cited by examiner

*Primary Examiner* — Gregory J Toatley
*Assistant Examiner* — Iyabo S Alli
(74) *Attorney, Agent, or Firm* — Lerner, David, Littenberg, Krumholz & Mentlik, LLP

(57) ABSTRACT

A method and a device for inspecting the quality of a formed thermoplastic fiber-reinforced plastic component wherein the component is tested by means of a sensor unit with a downstream electronic evaluation unit for analysis of the measuring result acquired by sensor technology by means of sample comparison, wherein by means of the optical sensor unit the surface roughness of the plastic component is measured after forming, which surface roughness is analyzed by means of the evaluation unit by a comparison with a stored reference pattern in such a manner that increased surface roughness is interpreted as increased internal materials porosity.

11 Claims, 1 Drawing Sheet

METHOD AND DEVICE FOR INSPECTING THE QUALITY OF A FORMED THERMOPLASTIC FIBER-REINFORCED PLASTIC COMPONENT

CROSS-REFERENCE TO RELATED APPLICATIONS

This application is a continuation of International Application No. PCT/EP2010/005156, filed Aug. 23, 2010, which claims the benefit of the filing date of German Patent Application No. 10 2009 038 746.3, filed on Aug. 27, 2009 and of U.S. Provisional Patent Application No. 61/237,384, filed on Aug. 27, 2009, the entire disclosures of which are hereby incorporated herein by reference.

TECHNICAL FIELD

The invention relates to a method and to a device for inspecting the quality of a formed thermoplastic fiber-reinforced plastic component that is tested by means of a sensor unit with a downstream electronic evaluation unit for analysis of the measuring result acquired by sensor technology.

The field of application of the invention predominantly relates to aircraft engineering. Fiber-reinforced plastic components are used in the manufacture of housing structures, wall structures and the like. Plastic components of interest in this context are predominantly reinforced with carbon fibers, thus forming so-called CFP components. Fiber-reinforced plastic components with a thermoplastic resin matrix are generally used as board-shaped semi-finished products and are brought to the desired shape by thermoplastic forming. For thermoplastic forming a press is used that provides the required forming pressure, and whose heated forming die reflects the final shape of the plastic component. As a result of thermoplastic forming, temperature differences can result in undesirable material separation or in increased porosity of the formed plastic component so that respective quality testing needs to be carried out after the forming process. This needs to take place by means of nondestructive testing of materials.

This problem is based on the thermal flow in the plastic component during the forming process. Prior to this process both the plastic component and the forming tool are heated. If the forming tool is not sufficiently hot, this will result in a heat flow from the component to the die during the forming process. The surface of the plastic component cools down first, whereas the interior of the plastic component cools down last. If the temperature of the plastic component is too low during the forming process, said porosity results.

From DE 102 58 336 B3 a method and a device for nondestructive materials testing is known, which method and device are also suitable for CFP components. In this method the plastic component to be tested is subjected to sound by means of an arrangement of ultrasound transducers. The ultrasound transducers are moved on a predetermined path relative to the plastic component and are acoustically coupled to the workpiece by means of a jet of liquid. This arrangement provides for amplification of the test transducers to be adjustable across a wide dynamic range, wherein both a monolithic range and a sandwich range of a CFP component can be tested for the quality of its materials.

However, such ultrasound testing requires considerable technical expenditure because in order to ensure acoustic coupling the jet of liquid needs to be generated, maintained and discharged. Furthermore, as a result of the inherent measuring principle, an ultrasound examination is quite time-consuming.

From DE 41 06 334 C1 a further method for testing the quality of fiber-reinforced plastic components by means of ultrasound is known. This method operates with image recording of echo pulses. At measuring points where the amplitude of the echo of a pulse penetrating the plastic component is below a predetermined value, the amplitude of any defect echo is recorded. While this method supports full-area examination of the plastic component with a single image, and thus in a single examination step, this method is also associated with the disadvantages inherent in the ultrasound examination explained above.

BACKGROUND TO THE INVENTION

It is thus the object of the present invention to create a method and a device for quality-testing fiber-reinforced plastic components with a thermoplastic matrix, which method and device with the use of simple technical means make it possible to examine the internal quality of the plastic components precisely and in a time-efficient manner.

The object is met on the basis of a method according to the precharacterising part of claim 1 in conjunction with its characteristic features. From the point of view of device technology, the object is met by claim 6. The respective related dependent claims state advantageous improvements of the invention.

The invention includes the process-related teaching according to which by means of an optical sensor unit the surface roughness of the plastic component is measured after forming, which surface roughness is analyzed by means of a downstream evaluation unit by a comparison with a stored reference pattern in such a manner that increased surface roughness is interpreted as increased internal materials porosity.

In other words the invention is based on analyzing a formed thermoplastic fiber-reinforced plastic component with reference to the surface roughness as to whether the interior quality of the plastic component has been diminished by the forming process. This represents a departure from directly examining the internal quality when assessing the internal quality. According to the invention, assessing the internal quality instead takes place on the basis of the external appearance of the plastic component. Since, with the use of data processing, optical acquisition and evaluation of the surface of a component by means of sample comparison can be effected very quickly in relation to the entire surface, very considerable time savings in the quality control can be achieved. Furthermore, no particular coupling between the sensor unit and the plastic component to be examined is required; in particular in contrast to ultrasound examination no liquid couplant needs to be used, and consequently the solution according to the invention is easier to implement from the point of view of equipment used. Standard components can be used for optical analysis. With the use of optical analysis, inferior internal quality can be deduced from a visibly rougher external surface than is the case in a fault-free plastic component. It has been observed that internal material separation and porosity manifest themselves as increased surface roughness on the plastic component. The invention thus uses this correlation between the surface and the internal quality.

As a particularly preferred measuring principle for implementing the method described above, optical strip reflection (reflectometry) is proposed. In this optical measuring method a strip pattern with luminous strips that are arranged straight and parallel and spaced apart from each other is generated by a radiation source, which strip pattern is projected onto the surface of the plastic component as the measurement object and is reflected from this surface. Due to the surface roughness the reflected strips are deformed. The deformed strips are acquired by a camera and are evaluated, by way of image analysis, in terms of surface angle, curvature and the like, in order to in this manner obtain conclusions relating to the distribution and the degree of surface roughness.

In the application of this measuring principle, which application forms the subject of the invention, it is proposed that the sensor unit comprises an LCD monitor for generating said strip pattern Immediately beside the aforesaid, and aligned in accordance with the optical axes, a CCD camera should be arranged for imaging the strip pattern reflected from the component surface. It is also possible to provide several sensor units in order to examine the plastic component simultaneously from several sides.

According to a preferred embodiment of the device according to the invention, a single sensor unit is, however, sufficient, which sensor unit is installed so as to be stationary, whereas by means of handling equipment the plastic component to be examined can be positioned so as to be flexible relative to the sensor unit. In this arrangement the handling equipment can be an industrial robot that can be moved along several spatial axes, which robot is present anyway, during the manufacturing process of the plastic component, for placing and removing the plastic component in or from the forming tool of the press.

By means of such a device the plastic component can be positioned in such a manner relative to the optical sensor unit that optical measuring can take place from several sides. Preferably, all the sides and thus the entire surface of the plastic component are optically measured in order to carry out a complete quality check. However, it is adequate if only those faces of the plastic component are optically measured, on which faces, based on experienced, reduced internal quality of the plastic component manifests itself by increased surface roughness. By means of this measure the time required for inspection can be further reduced.

According to another measure improving the invention, it is proposed that the stored reference pattern is generated in such a manner by way of the optical sensor unit that a sample component with normal surface roughness is optically measured by said optical sensor unit. The data measured in this manner is stored as a type of image file in a storage unit of the evaluation unit, which is preferably designed as a computer (PC).

In order to carry out an unequivocal inspection, according to another measure improving the invention it is proposed to determine a threshold value relating to the surface roughness of the plastic component. If, after implementation of the comparison of the measured surface roughness with the stored reference pattern, this threshold value is exceeded, as part of an automated quality inspection a good/bad selection of the plastic components to be checked can be made. In this manner an unequivocal and uniform inspection result can be achieved.

The solution according to the invention provides the conditions for the optical sensor unit to be able to detect local changes in the surface roughness relating to the overall surface of a measured face of the plastic component. If locally there is increased surface roughness, from this, locally inferior internal quality of the plastic component can be deduced.

BRIEF DESCRIPTION OF THE DRAWINGS

Below, further measures that improve the invention, together with the description of a preferred exemplary embodiment, are provided in more detail with reference to the figures. The following are shown.

DETAILED DESCRIPTION OF EXEMPLARY EMBODIMENTS

Figure 1:
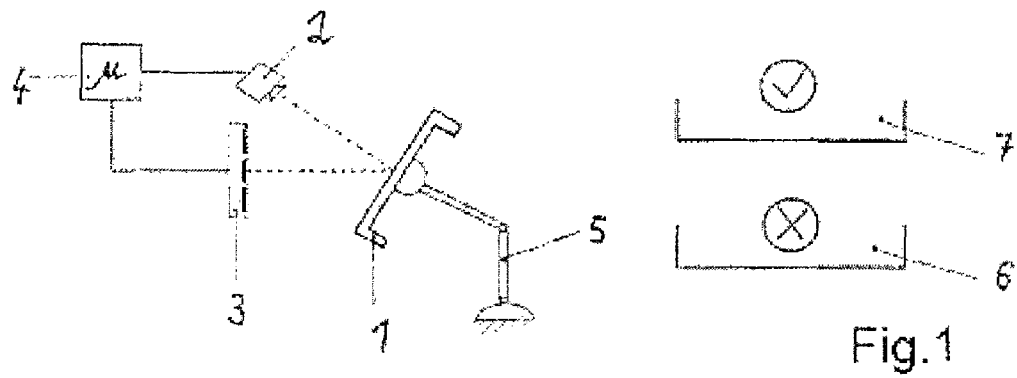
FIG. 1 a device for inspecting the quality of a formed thermoplastic fiber-reinforced plastic component, FIG. 2 a diagrammatic top view of local changes of the surface roughness relating to the overall surface of a plastic component, and FIG. 3 a cross section A-A of the region of increased surface roughness shown in FIG. 2.

According to FIG. 1 the device for checking the quality of a fiber-reinforced plastic component 1 thermoplastically formed in the preceding manufacturing step, which plastic component 1 is a CFP material, comprises a sensor unit 2 for optically inspecting the plastic component 1, which sensor unit 2 is designed as a CCD camera. Adjacent to the sensor unit 2 an LCD monitor 3 for generating a strip pattern is positioned. The LCD monitor 3 emits the strip pattern in such a manner in the direction of the surface of the plastic component 1 that the image reflected from it is positioned on the optical axis of the sensor unit 2, in other words can be captured by the aforesaid. As a result of irregular surfaces the reflected strip pattern comprises information relating to the surface roughness of the plastic component 1. This image information is evaluated by a downstream evaluation unit 4 by means of a comparison with a saved and stored reference pattern with the use of image analysis. The fact that increased surface roughness is interpreted as increased internal materials porosity forms the basis of the evaluation.

Relative positioning of the plastic component 1 to the sensor unit 2 with an LCD monitor 3 takes place by way of handling equipment 5 which in the present case is in the form of an industrial robot that otherwise is used for handling the plastic component 1.

If as a result of the comparison by the evaluation unit 4 the plastic component to be checked is classified as a reject, the handling equipment 5 places this reject into a rejects box 6. Otherwise the acceptable part is placed into a supplies box 7.

Figure 2:
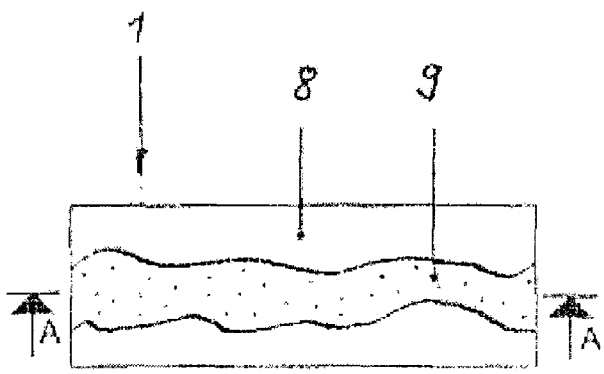
Figure 3:
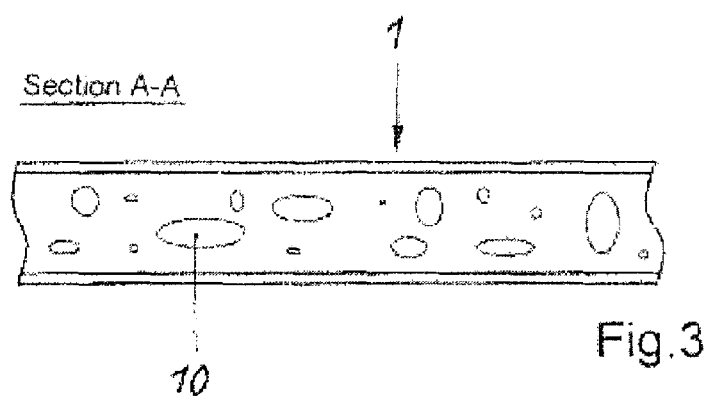

FIG. 2 shows a plastic component 1 that apart from a region 8 of normal surface roughness comprises a region 9 of significantly increased surface roughness. The surface roughness of the region 9 is both visible and apparent when touched. Below the region 9, according to FIG. 3 (section A-A) there are many pores 10, which means that there is considerable internal materials porosity. With this increased internal materials porosity the strength of the plastic component 1 is inadmissibly compromised so that this plastic component 1 is to be set aside as a reject.

In addition, it should be pointed out that "comprising" does not exclude other elements or steps, and "a" or "one" does not exclude a plural number. Furthermore, it should be pointed out that characteristics or steps which have been described with reference to one of the above exemplary embodiments can also be used in combination with other characteristics or steps of other exemplary embodiments described above. Reference characters in the claims are not to be interpreted as limitations.

LIST OF REFERENCE CHARACTERS

1 Plastic component
2 Sensor unit
3 LCD monitor
4 Evaluation unit

5 Handling equipment
6 Rejects box
7 Supplies box
8 Region of normal surface roughness
9 Region of increased surface roughness
10 Pores

The invention claimed is:

1. A method for inspecting the quality of a formed thermoplastic fiber-reinforced plastic component, the method comprising:
measuring by a sensor unit comprising an optical sensor unit, the surface roughness of the plastic component after forming; and
analyzing the measured surface roughness by an evaluation unit downstream of the sensor unit by comparing the measured surface roughness with a stored reference pattern,
wherein an increased surface roughness is indicative of an increased internal materials porosity.

2. The method of claim 1, further comprising detecting by the sensor unit, local changes in the surface roughness relative to the overall surface of the measured face of the plastic component.

3. The method of claim 1, further comprising optically measuring a plurality of faces of the plastic component.

4. The method of claim 1, further comprising obtaining the stored reference pattern by the optical sensor unit by optically measuring the normal surface roughness of a sample component.

5. The method of claim 1, further comprising defining a threshold value relating to the surface roughness of the plastic component to make a good/bad selection during an automated quality inspection.

6. A device for inspecting the quality of a formed thermoplastic fiber-reinforced plastic component comprising:
a sensor unit for checking the plastic component, the sensor unit comprising an optical sensor;
an electronic evaluation unit for analysis of the measuring result acquired by the sensor unit and configured for sample comparison and arranged downstream of said sensor unit,
wherein the optical sensor unit is configured to measure the surface roughness of the plastic component after forming,
wherein the evaluation unit is configured to analyze the measured surface roughness by a comparison with a stored reference pattern wherein an increased surface roughness is indicative of increased internal materials porosity.

7. The device of claim 6, wherein the sensor unit is configured to determine the surface roughness of the plastic component after forming by the measuring principle of optical strip reflection.

8. The device of claim 7, further comprising an LCD monitor associated with the sensor unit for generating a strip pattern.

9. The device of claim 7, wherein the sensor unit is configured as a CCD camera for imaging the strip pattern reflected from the component surface.

10. The device of claim 6, wherein the sensor unit is installed so as to be stationary, whereas the plastic component to be examined is configured to be positioned by a handling equipment so as to be movable relative to the sensor unit.

11. The device of claim 6, wherein the fiber-reinforced plastic component to be checked, which plastic component has been formed by pressing, comprises a CFP material comprising a thermoplastic matrix.

* * * * *

UNITED STATES PATENT AND TRADEMARK OFFICE
CERTIFICATE OF CORRECTION

PATENT NO. : 8,467,069 B2  
APPLICATION NO. : 13/403386  
DATED : June 18, 2013  
INVENTOR(S) : Klaus Edelmann et al.

Page 1 of 1

It is certified that error appears in the above-identified patent and that said Letters Patent is hereby corrected as shown below:

In the Specification,

Column 3, line 11, after "pattern" insert -- . --.

Signed and Sealed this
Fifteenth Day of September, 2015

Michelle K. Lee
*Director of the United States Patent and Trademark Office*